US007776602B2

(12) United States Patent
Reznek et al.

(10) Patent No.: US 7,776,602 B2
(45) Date of Patent: *Aug. 17, 2010

(54) METHODS OF PROVIDING PRODUCT CONSISTENCY

(75) Inventors: Steven R. Reznek, Concord, MA (US); Ian D. Morrison, Acton, MA (US); Meng-Jiao Wang, Lexington, MA (US); Steven E. Brown, Tyngsboro, MA (US); Martin C. Green, Boxboro, MA (US); William L. Sifleet, Clinton, MA (US); Lawrence J. Murphy, Bedford, MA (US)

(73) Assignee: Cabot Corporation, Boston, MA (US)

( * ) Notice: Subject to any disclaimer, the term of this patent is extended or adjusted under 35 U.S.C. 154(b) by 1147 days.

This patent is subject to a terminal disclaimer.

(21) Appl. No.: 10/649,347

(22) Filed: Aug. 27, 2003

(65) Prior Publication Data

US 2004/0197923 A1  Oct. 7, 2004

Related U.S. Application Data

(60) Provisional application No. 60/459,230, filed on Apr. 1, 2003, provisional application No. 60/485,964, filed on Jul. 10, 2003, provisional application No. 60/485,965, filed on Jul. 10, 2003, provisional application No. 60/491,632, filed on Jul. 31, 2003.

(51) Int. Cl.
  *G01N 31/00* (2006.01)
(52) U.S. Cl. ............................. 436/2; 436/145; 73/53.01
(58) Field of Classification Search ...................... 436/2, 436/145; 73/53.01
  See application file for complete search history.

(56) References Cited

U.S. PATENT DOCUMENTS

| | | | |
|---|---|---|---|
| 3,229,507 A | 1/1966 | Sljaka et al. ................... 73/59 |
| 3,659,896 A | 5/1972 | Smith et al. .................... 296/93 |
| 4,071,496 A | 1/1978 | Kraus et al. ............... 260/42.36 |
| 4,088,628 A | 5/1978 | Bernstein et al. ......... 260/42.46 |
| 4,093,421 A | 6/1978 | Jerkins ....................... 23/259.5 |
| 4,255,296 A | 3/1981 | Ogawa et al. .................. 260/5 |
| 4,259,218 A | 3/1981 | Haws ............................ 260/5 |
| 4,360,627 A | 11/1982 | Okado et al. ................ 524/496 |
| 4,478,973 A | 10/1984 | Misono et al. ............... 524/496 |
| 4,540,560 A | 9/1985 | Henderson et al. .......... 423/445 |
| 4,548,980 A | 10/1985 | Nagata et al. ............... 524/495 |
| 4,678,830 A | 7/1987 | Sato et al. ................... 524/495 |
| 4,690,965 A | 9/1987 | Hirata et al. ................ 524/236 |
| 4,721,740 A | 1/1988 | Takeshita et al. ............ 523/215 |
| 4,878,379 A | 11/1989 | Deer ............................. 73/60 |
| 4,914,147 A | 4/1990 | Mouri et al. ................ 524/495 |
| 4,992,190 A | 2/1991 | Shtarkman ............... 252/62.52 |
| 5,093,407 A | 3/1992 | Komai et al. ................ 524/495 |
| 5,124,396 A | 6/1992 | Branan, Jr. et al. .......... 524/496 |
| 5,128,395 A | 7/1992 | Terakawa et al. ............ 524/274 |
| 5,162,421 A | 11/1992 | Ue et al. ...................... 524/495 |
| 5,190,739 A | 3/1993 | MacKay et al. ............. 423/450 |
| 5,194,488 A | 3/1993 | Piestert et al. ............... 524/703 |
| 5,211,932 A | 5/1993 | Blaylock et al. ............. 423/450 |
| 5,231,129 A | 7/1993 | Misono ....................... 524/496 |
| 5,232,974 A | 8/1993 | Branan, Jr. et al. .......... 524/495 |
| 5,288,788 A | 2/1994 | Shieh et al. .................. 524/495 |
| 5,292,790 A | 3/1994 | Shimizu et al. ............. 524/496 |
| 5,303,578 A | 4/1994 | Williams et al. ........... 73/54.24 |
| 5,310,777 A | 5/1994 | Sekido et al. ................ 524/496 |
| 5,321,072 A | 6/1994 | Misono ....................... 524/496 |
| 5,322,724 A | 6/1994 | Levens ........................ 428/57 |
| 5,322,874 A | 6/1994 | Fujii et al. ................... 524/227 |
| 5,352,289 A | 10/1994 | Weaver et al. ............... 106/476 |
| 5,362,794 A | 11/1994 | Inui et al. .................... 624/496 |
| 5,382,621 A | 1/1995 | Laube ......................... 524/496 |
| 5,405,623 A | 4/1995 | Barkalow et al. ............... 426/5 |
| 5,426,148 A | 6/1995 | Tucker ........................ 524/496 |
| 5,428,099 A | 6/1995 | Morrar et al. ............... 524/495 |
| 5,430,087 A | 7/1995 | Carlson et al. .............. 524/496 |
| 5,480,626 A | 1/1996 | Klasen et al. ............. 423/449.1 |
| 5,534,578 A | 7/1996 | Wideman et al. ........... 524/396 |
| 5,547,609 A | 8/1996 | Fujii et al. .................... 252/511 |
| 5,620,824 A * | 4/1997 | Okado et al. ............. 430/108.6 |
| 5,639,817 A | 6/1997 | Probst et al. ................ 524/496 |
| 5,643,991 A | 7/1997 | Stipe et al. .................. 524/496 |
| 5,652,298 A | 7/1997 | Murray ....................... 524/571 |
| 5,688,317 A | 11/1997 | MacKay et al. ............. 106/476 |
| 5,696,197 A | 12/1997 | Smith et al. ................. 524/495 |
| 5,705,555 A | 1/1998 | Guilfoy et al. .............. 524/495 |
| 5,714,096 A | 2/1998 | Dorfman .................... 252/511 |
| 5,723,531 A | 3/1998 | Visel et al. .................. 524/496 |

(Continued)

FOREIGN PATENT DOCUMENTS

EP        0253290        1/1988

(Continued)

OTHER PUBLICATIONS

Attachment A—Development History.

(Continued)

*Primary Examiner*—Lyle A Alexander

(57) ABSTRACT

The present invention relates to a method of providing product consistency of a particulate material or the product containing the same, by measuring and/or analyzing at least one interfacial potential property value of the particulate material. The method may be used as a QA/QC method to insure product consistency.

22 Claims, 1 Drawing Sheet

U.S. PATENT DOCUMENTS

| | | | |
|---|---|---|---|
| 5,733,480 A | 3/1998 | Lee et al. | 252/511 |
| 5,792,941 A | 8/1998 | Rye et al. | 73/53.01 |
| 5,801,209 A | 9/1998 | Chung et al. | 521/99 |
| 5,859,120 A | 1/1999 | Karl et al. | 524/495 |
| 5,877,250 A | 3/1999 | Sant | 524/496 |
| 5,877,251 A | 3/1999 | Sant | 524/496 |
| 5,974,167 A | 10/1999 | Reszler | 382/141 |
| 6,013,737 A | 1/2000 | Takagishi et al. | 525/332.7 |
| 6,046,266 A | 4/2000 | Sandstrom et al. | 524/492 |
| 6,056,933 A | 5/2000 | Vogler et al. | 423/449.1 |
| 6,084,015 A | 7/2000 | Chino et al. | 524/189 |
| 6,086,792 A | 7/2000 | Reid et al. | 252/511 |
| 6,096,833 A | 8/2000 | Araki et al. | 525/342 |
| 6,099,818 A | 8/2000 | Freund et al. | 423/449.1 |
| 6,107,538 A * | 8/2000 | Young et al. | 604/369 |
| 6,156,837 A | 12/2000 | Branan, Jr. et al. | 524/495 |
| 6,197,277 B1 | 3/2001 | Fukuda et al. | |
| 6,201,059 B1 * | 3/2001 | Wideman et al. | 524/518 |
| 6,228,928 B1 | 5/2001 | Soeda et al. | 524/495 |
| 6,277,350 B1 | 8/2001 | Gerspacher | 423/449.1 |
| 6,391,274 B1 | 5/2002 | Vogler et al. | 423/275 |
| 6,410,630 B1 | 6/2002 | Hoover et al. | 524/365 |
| 6,448,309 B2 | 9/2002 | Mahmud et al. | 523/215 |
| 6,800,413 B2 * | 10/2004 | Barthel et al. | 430/108.3 |
| 2001/0036995 A1 | 11/2001 | Mahmud et al. | 524/495 |
| 2002/0077409 A1 | 6/2002 | Sakaki et al. | 524/496 |
| 2002/0107318 A1 | 8/2002 | Yamada et al. | 524/495 |
| 2002/0156177 A1 | 10/2002 | Freund | 524/496 |
| 2002/0173582 A1 | 11/2002 | Schmidt | 524/504 |
| 2003/0097871 A1 | 5/2003 | Mansky | 73/64.49 |
| 2003/0162876 A1 | 8/2003 | Vanier et al. | 524/437 |
| 2003/0164027 A1 | 9/2003 | Terrom | 73/64.48 |

FOREIGN PATENT DOCUMENTS

| | | |
|---|---|---|
| EP | 0453625 | 10/1991 |
| GB | 2378716 | 2/2003 |
| JP | 2002-297942 | 10/2002 |
| WO | WO 01/46883 A2 | 6/2001 |

OTHER PUBLICATIONS

Strom, "Wetting studies related to offset printing," vol. 50-04C, pp. 768 (1988) Abstract only.

Tikhonov, "On the evaluation of the work of adhesion, cohesion, and surface tension of high-viscous and solid bodies," Kolloidn Zh, vol. 53, No. 3, pp. 552-558 (1991) Abstract only.

Janczuk, et al., "Surface free energy components and adsorption properties of some porous glasses," Mater Chem Phys. vol. 25, No. 2, pp. 185-198 (1990) Abstract only.

Janczuk, et al., "Surface free energy of celestite and its flotation activity," Colloids Surf. vol. 35, No. 1, pp. 41-48 (1989) Abstract only.

Wojcik et al., "Gas-adsorption studies on correlations between the flotability of minerals and the work of water adhesion to their surfaces," Colloids Surf. vol. 30, No. 3-4, pp. 275-285 (1988) Abstract only.

Lipatov, "Adhesion at the polymer mixtures-solid interface," Vide, Couches Minces, vol. 50 (274), pp. 415-420 (1994) Abstract only.

Hill, "Wall slip in polymer melts: A pseudo-chemical model," J. Rheol. vol. 42, No. 3, pp. 581-601 (1998) Abstract only.

Scheie, "The upward force on liquid in a capillary tube," Am. J. Phys. vol. 57, No. 3, pp. 278-289 (1989) Abstract only.

Lee et al., "Effects of polymer-filler interaction on the mechanical properties of nylon 6,6 filled with organosilane-treated fillers," J. Adhes. Sci. Technol., vol. 3, No. 4, pp. 291-303 (1989) Abstract only.

Abramzon et al., "Determination of the work of adhesion and cohesion" ZH. Prikladnoi Khim, vol. 53, No. 5, pp. 1040-1043 (1980) Abstract only.

Mangipudi et al., Direct measurement of molecular level adhesion between poly(ethylene terephthalate) and polyethylene films: Determination of surface and interfacial energies, J. Adhesion Sci. Technol., vol. 8, No. 11, pp. 1251-1270 (1994) Abstract only.

Owen, "Surface properties of silicone release coatings," Proc. First Internat. Congress on Adhesion Science and Technology, pp. 255-263 (1995) Abstract only.

Kaya, The effect of pore fluid contamination on a selected physicochemical parameters of fine grained soils (Adsorption, Conductivity), vol. 57-05B, p. 3354 (1996) Abstract only.

Qin, Adhesion properties of polymeric materials (Asphalts, Cohesion), vol. 57-02B, p. 1260 (1995) Abstract only.

Stepanov, "Electrocapillary behaviour of liquid bismuth in binary melts of strontium chloride with sodium and cesium chlorides," Ehlektrokhimiya, vol. 30, No. 8, pp. 1032-1038 (1994) Abstract only.

Kulawik, et al., "Kinetics of the molecular interactions in some extraction system," ISEC '88 International solvent extraction Conference, vol. 2, pp. 77-78 (1988) Abstract only.

Nardin et al., "Stress transfer analysis in fibre/elastomer interfaces," Comptes-Rendus des Huitiemes Journess Nationales sur les Composites, pp. 289-300 (1992) Abstract only.

Maugis, "Adherence and Fracture Mechanics," Adhesive Bonding, pp. 303-335 (1991) Abstract only.

Wan et al., "Surface forces at crack interfaces in mica in the presence of capillary condensation," Acta Metallurgia et Materialia, vol. 38, No. 11, pp. 2073-2083 (1990) Abstract only.

Savenko et al., "Effect of diamond-like carbon coatings on the mechanical properties of subsurface layers of single crystals of silicon," Physics and Chemistry of Materials Treatment, vol. 31, No. 2, pp. 149-153 (1997) Abstract only.

Lellig et al., "Glass and polymer: wetting and adhesion," Glass Science and Technology, vol. 69, No. 11, pp. 357-367 (1996) Abstract only.

Maugis, "Adherence of elastomers: fracture mechanics aspects," Journal of Adhesion, vol. 23, No. 1, pp. 61-66 (1987) Abstract only.

Riande et al., "Fundamental aspects of the adhesion of polymers," Revista de Plasticos Modernos, vol. 80, No. 530, pp. 170-179 (2000) Abstract only.

Gilbert, "Surface treatments for particulate fillers in plastics," Plastics Additivies. An A-Z reference, pp. 590-603 (1998) Abstract only.

Maltese, "Interfacial energy between polymers," Materie Plastiche ed Elastomeri, VBol. 64, Nos. ½, pp. 74-78 (1999) Abstract only.

Cherry et al., "Predicting work of adhesion using molecular modeling," Adhesion '96, Conference Proced., vol. 1, pp. 299-304 (1996) Abstract only.

Feinerman et al., "Rule of interfacial equilibrium," J. Adhesion, vol. 60, Nos. 1-4, pp. 99-112, (1997) Abstract only.

Geraghty et al., "Investigation of parameters influencing bioadhesive properties of myverol 18-99/water gels," Biomaterials, vol. 18, No. 1, pp. 63-67 (1997) Abstract only.

Wimolkiatisak et al., Directly paintable, high adhesion polyolefin compounds, Plast' 21 No. 43, pp. 44-47 (1995) Abstract only.

Drzal, et al., "Adhesion of carbon fibres to polycarbonate matrices: interphase composition and structure," Antec '95. vol. II, Conference Proceedings, pp. 2877-2881 (1995) Abstract only.

Moore, "Wetting in rubber-to-metal bonding agents," Rubb. Plast. News, vol. 24, No. 7, pp. 17-18 (1994) Abstract only.

Mangipudi et al., "Adhesion of thin polymer films: Effects of surface and interfacial energies and rheological properties," Antec '93 Conference Proceedings, vol. III, pp. 3099-3100, (1993) Abstract only.

Bautista et al., "Surface characterization of polypropylene used as a matrix in composite materials," Rev. Plast. Mod. vol. 66, No. 449, pp. 505-509 (1993) Abstract only.

Pritykin et al., "New thermodynamic characteristics of polymer adhesive properties," International Adhesion Conference, p. 11.1-3 (1984) Abstract only.

Moskvitin, Physiocochemical Principles of Gluing and Adhesion processes, NSF, Rpt. No. SFCSI-Agr (TT-68-50368, p. 197 (1969) Abstract only.

Mayne, "Further developments with epoxy/polyamine films," Corros. Sci., vol. 35, Nos. 5/8, pp. 1359-1361 (1993) Abstract only.

Padday, "Spreading, wetting, and contact angles," J. Adhes. Sci. Tech., vol. 6, No. 12, pp. 1347-1358 (1992) Abstract only.

Mark, "Future improvements in cohesive and adhesive strength of polymers. I.," Adhesives Age, vol. 22, No. 7, pp. 35-40 (1979) Abstract only.

Hansen, "The three dimensional solubility parameter—key to paint component affinities: I. Solvents, Plasticizers, Polymers, and Resins," Journal of Paint Technology, vol. 39, No. 505, pp. 104-117 (1967).

Hansen, "The three dimensional solubility parameter—key to paint component affinities: II and III-II. Solvents, Plasticizers, Polymers, and Resins," Journal of Paint Technology, vol. 39, No. 511, pp. 505-510 (1967).

Hansen, "III. Independent calculation of the parameter components," Journal of Paint Technology, vol. 39, No. 511, pp. 511-514 (1967).

Hansen et al., "On the use of cohesion parameters to characterize surfaces," J. Adhesion, vol. 15, pp. 275-286 (1983).

Hansen, "Cohesion parameters for surfaces, pigments, and fillers," Surface Coatings International vol. 8, pp. 386-391, (1997).

Shareef et al., "Suspension interaction of pigments in solvents: characterization of pigment surfaces in terms of three-dimensional solubility parameters of solvents," Journal of Coatings Technology, vol. 58, No. 733, pp. 35-44 (1986).

Vinther, "Application of the concepts solubility parameter and pigment charge," Chemie des Peintures Engl. vol. 34, No. 10, pp. 363-372 (1971).

Schreiber, "Solvent balance, dispersion and rheological properties of pigmented polymer compositions," Journal of Paint Technology, vol. 46, No. 598, pp. 35-39 (1974).

Burrell, "The challenge of the solubility parameter concept," Journal of Paint Technology, vol. 40, No. 520, pp. 197-208 (1968).

Trudgian, "The pattern of solvent-resin-pigment affinities," Official Digest, Presented at the 41$^{st}$ Annual Meeting of the Federation of Societies for Paint Technology, pp. 1210-1231 (1963).

Schroder, Colloid chemistry aids to formulating inks and paints, Harmonization of the energetics of raw materials by using the solubility parameter concept, vol. 5, No. 98, pp. 334-340 (no date).

Chasey, "Methods for evaluating oil/polymer interactions in carbon black filled compounds," Rubber World, pp. 35-40 (1993).

Wolff, et al., "Filler-elastomer interactions. Part VII. Study on bound rubber," Rubber Chemistry and Technology, vol. 66, No. 2, pp. 163-177 (1993).

Barton, "CRC Handbook of solubility parameters and other cohesion parameters," pp. 1-21, (1991).

Kaya, et al., "Interfacial parameters and work of adhesion in soil-liquid systems," Geotechnical Testing Journal, vol. 23, No. 4, pp. 464-471 (2000).

Skaarup, "The three dimensional solubility parameter and its use—II. Pigmented Systems," pp. 28-42 (no date).

Grubenmann, "The solvent dependence of the solubility of organic solids, and solubility parameter theory: investigation by means of an organic pigment," Dyes and Pigments, vol. 21, pp. 273-292 (1993).

Hodne et al., "The Effect of the Cement Zeta Potential and Slurry Conductivity on the Consistency of Oilwell Cement Slurries," Cement and Concrete Research, vol. 30, pp. 1767-1772, 2000.

"Bound Rubber and Carbon Black Reinforcement," by E. M Dannenberg, 1986, pp. 512-524.

"Filler-Elastomer Interactions. Part VII. Study on Bound Rubber," by Siegfried Wolff et al., reprinted from Rubber Chemistry and Technology, vol. 66, No. 2, May-Jun. 1993, 163-177.

"Standard Test Method for Carbon Black—Iodine Adsorption Number," ASTM Designation D 1510-99, pp. 271-275.

"Standard Test Method for Carbon Black—CTAB (Cetyltrimethylammonium Bromide) Surface Area," ATSM Designation D 3765-99, pp. 563-568.

"Standard Test Methods for Carbon Black—Surface Area by Multipoint B.E.T. Nitrogen Adsorption," ATSM Designation D 4820-97, pp. 763-769.

"Standard Test Methods for Carbon Black—External Surface Area by Multipoint Nitrogen Adsorption," ATSM Designation D 5816-96, pp. 878-880.

"Standard Test Method for Carbon Black—Total and External Surface Area by Nitrogen Adsorption," ATSM Designation D 6556-00a, pp. 970-974.

"Roles of Work of Adhesion between Carbon Blacks and Thermoplastic Polymers on Electrical Properties of Composites," by Soo-Jin Park et al., published in the Journal of Colloid and Interface Science 255, pp. 145-149 (2002).

"Component Interactions and the Stability of Some Pigment/Polymer Dispersions," by P. Mukhopadhyay et al., published in the Journal of Applied Polymer Science, vol. 67, pp. 245-253 (1998).

"Adhesion and Components of Solid Surface Energies," by John H. Clint, published in Current Opinion in Colloid & Interface Science 6, pp. 28-33 (2001).

"Estimation of the Reliability of Hansen-Parameters of Photooxidative Degraded Polymer Films by Contact Angle Measurements," by Anita Horn et al., Hildesheim, Germany, pp. 1-12.

"Basic and Acidic Surface Oxides on Carbon Fiber and Their Influence on the Expected Adhesion to Polyamide," by A. Bismarck et al., published in Colloids and Surfaces, A: Physiochemical and Engineering Aspects 159, pp. 341-350 (1999).

* cited by examiner

METHODS OF PROVIDING PRODUCT CONSISTENCY

This application claims the benefit under 35 U.S.C. §119(e) of prior U.S. Provisional Patent Application No. 60/459,230 filed Apr. 1, 2003, 60/485,964 filed Jul. 10, 2003, 60/485,965 filed Jul. 10, 2003, and 60/491,632 filed Jul. 31, 2003, which are all incorporated in its entirety by reference herein.

BACKGROUND OF THE INVENTION

The present invention relates to methods for providing product consistency for particulate materials.

In general, products of the chemical industry fall into one of two types—formulaic chemicals and performance chemicals. Formulaic chemicals are defined by their composition. If they are sold in different grades, the grades are distinguished by the concentration of impurities. Examples include ammonia, benzene, carbon tetrachloride, diethyl ether, and formaldehyde. Performance chemicals, which include polymers, dyes, pigments, and fragrances, are valued because of what they do, not what their composition is. Important types of performance chemicals include fine particle products such as carbon black, silica, titania, tantalum, calcium carbonate which are used in applications including reinforcement, rheology, color, and conductivity.

In order to insure consistency, specifications are set for fine particle products. Typically these specifications will include one or more measures of morphology and may further include one or more measures of chemical constituents. Common measures of morphology are particle size, surface area, structure, porosity, aggregate size, and aggregate shape. Common measures of chemistry include bulk and surface composition as well as analyses of extractable species. Measurements of variability of these properties can be made either during manufacturing to insure the process remains in control (often referred to as quality control, or QC) or on the product prior to shipment (often referred to as quality assurance, or QA).

For example, carbon black is typically sold with at least one morphological specification, which may be surface area, particle size, structure, and porosity. Performance tests, such as, for example, bound rubber or compound moisture absorption (CMA) tests may also be run, depending on the intended use for the carbon black.

Despite these quality control and quality assurance (QC/QA) efforts, it is not unusual for a customer to complain that a batch of product received did not perform as expected, despite being "within spec". For example, variations in the rate of rubber cure, the appearance of white haze on molded rubber parts, low thixotropy in adhesives, and variations in plastic compounding times have all been traced back to lot-to-lot variations of carbon blacks even when each lot was within specification. This often results in the producer undertaking a thorough and costly study of the process and product and trying to make adjustments so that the product once again performs as expected.

Determining why a product did not perform as expected is inefficient and often both time consuming and expensive. It involves evaluation to assess why a problem has occurred rather than avoiding the problem in the first place. Many times, the producer will adjust manufacturing steps, not understanding the result but only in an attempt to change the product somehow to see a product difference. At times, this amounts to guess work.

Therefore, there is a need, especially in the particulate material industry, for methods in which product consistency can be routinely insured.

SUMMARY OF THE INVENTION

The present invention relates to a method of providing product consistency which comprises the steps of: a) maintaining at least one morphological value of a particulate material within a first target range; and b) maintaining at least one interfacial potential property value of the particulate material within a second target range. In one embodiment, the step of maintaining at least one morphological value comprises i) determining at least one morphological value of the particulate material and ii) if necessary, adjusting at least one process variable of a process for producing the particulate material. In another embodiment, the step of maintaining at least one interfacial potential property value comprises i) determining at least one interfacial potential property value of the particulate material; and ii) if needed, adjusting at least one process variable of a process for producing the particulate material. For either embodiment, the adjustment maintains the corresponding value within the corresponding target range.

The present invention further relates to a method of controlling a process for producing a particulate material comprising the steps of: a) determining at least one morphological value of the particulate material and at least one interfacial potential property value of the particulate material; b) comparing the morphological value and the interfacial potential property value of the particulate material to a target morphological value and a target interfacial potential property value; and c) if necessary, adjusting at least one process variable for the process.

The present invention further relates to a method of producing a target particulate material having at least one target morphological value and at least one target interfacial potential property value, wherein the method comprises the steps of: a) producing a sample particulate material having the target morphological value of the target particulate material; b) determining at least one interfacial potential property value of the sample particulate material; c) determining the difference between the interfacial potential property value of the sample particulate material and the target interfacial potential property value of the target particulate material; d) if necessary, adjusting at least one process variable of the process; e) if necessary, repeating steps a)-d) until the difference between the interfacial potential property value of the sample particulate material and the target interfacial potential property value of the target particulate material is less than or equal to a target delta; and f) producing the target particulate material having the target morphological value and the target interfacial potential property value using the adjusted process variables.

The present invention further relates to a method for quality control comprising analyzing at least one interfacial potential property value of a particulate material on a routine basis to insure quality control.

The present invention further relates to a method for quality assurance comprising analyzing at least one interfacial potential property value in a particulate material on a routine basis prior to shipment to a customer to insure quality assurance.

The present invention further relates to a quality control system comprising a test for determining at least one interfacial property value of a particulate material and a device or medium to record said at least one interfacial potential property value of said particulate material.

It is to be understood that both the foregoing general description and the following detailed description are exemplary and explanatory only and are intended to provide further explanation of the present invention, as claimed.

DETAILED DESCRIPTION OF THE INVENTION

Figure 1:
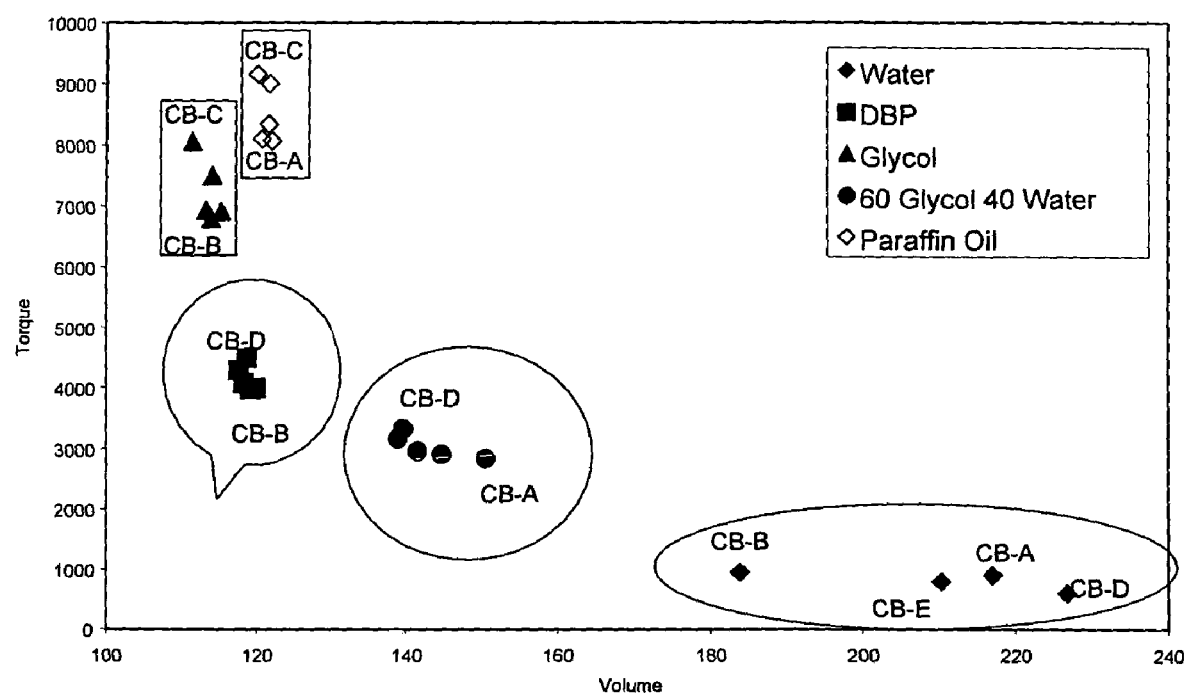
FIG. 1 shows the maximum torque versus volume for the same grade of carbon black using various probe liquids.

The present invention relates to a method of providing product consistency. In more detail, the present invention relates to quality control and/or quality assurance systems and methods of maintaining quality control and/or quality assurance.

Particulate materials such as fillers and pigments are made within defined specifications but even doing so it has been found that the product at times would not perform consistently in the customer's application. Until now, the industry was not entirely clear why the product would not perform consistently even though it was within morphological specifications. Thus, until now, there was a major portion of quality control and quality assurance missing from the industry and/or the technology area. The present invention now makes it possible to maintain the same product within specifications, thereby providing to the customer a product that should perform consistently in their end product. Thus, the present invention not only affects the particulate material being made and has benefits to the particulate material being made, the present invention further has beneficial effects downstream such as permitting consistent end product performance wherein the particulate material is present in the end product. Thus, the present invention not only provides quality control and/or quality assurance for the particulate material but may also make it easier for a customer to obtain consistency in their product and any intermediate products containing the particulate material, such as polymer products, elastomeric products, inks, coatings, toners, and the like.

The method of the present invention involves the steps of maintaining at least one morphological value within a target range and maintaining at least one interfacial potential property value with a target range. The steps can be in any order. As used herein, "maintaining" can include measuring or analyzing for the stated property and determining whether that value falls within the desired target ranges. If it does, the value is said to be within specifications and is therefore maintained. If it does not, in order to keep the value maintained, some change is made in the process used to prepare the particulate material such that the value is brought back within range. In this way, the method of the present invention provides for product consistency by utilizing a system consisting of sampling, testing, comparison, selection, and optional process adjustment so that the product performs substantially the same.

Thus, the method of the present invention can be considered to be a quality assurance method and/or a quality control method. Quality assurance can include the steps of sampling a product periodically, making one or more measurements on the product, comparing the results of these measurement(s) with expected or target value(s), and then releasing the product based on sufficient agreement with the expected or target value(s). Quality control can include the steps of sampling a product periodically, making one or more measurements on the product, comparing the results of these measurement(s) with expected or target value(s), transforming the measurement(s) by means of formula(e) or algorithm(s) to determine if any operation in a production process needs to be changed, changing the production process appropriately, and repeating these steps until the product meets expected value(s).

Both the step of maintaining at least one morphological value and the step of maintaining at least one interfacial potential property value of the present invention are done routinely, that is, they are performed as a regular part of the manufacturing process and are done prior to a customer receiving the product. Thus, the method of present invention is a quality control and/or a quality assurance method in that measurements are made periodically on the product and the results compared to target value ranges prior to a customer ever receiving the product. In more detail, one or more embodiments of the present invention relate to testing of the interfacial potential property in order to maintain a consistent product. Thus, one aspect of some embodiments of the present invention involves the routine testing of the particulate material being made or already produced in order to insure that the product is consistent with respect to the interfacial potential property and optionally the morphological property. Preferably, the routine testing of the interfacial potential property promotes and provides a consistent performance of the particulate material in its use by a customer and its performance in the final product and any intermediate product. Routine testing can include testing for the interfacial potential property in particulate material at regular time intervals, such as every hour or portion thereof, multiple hours, every day, every week, and the like. The routine testing can, in combination or in the alternative, be with respect to every batch or partial batch made of the particulate material. The routine testing can, alternatively or in combination, include testing for the interfacial potential property with respect to intervals of amounts of material produced. For instance, every 1,000 pounds of the particulate material produced will trigger the test for interfacial potential. Needless to say, the amounts of material produced that would trigger the testing for interfacial potential properties can be decided by the manufacturer or customer. Also, routine testing in the alternative or in combination can be done prior to shipping. As can be seen, from the above, routine testing generally involves testing for the interfacial potential property before any problem is uncovered and is done for purposes of quality control and/or quality assurance. The testing for the interfacial potential to insure product performance and to insure a consistent product in the embodiments of the present invention, avoids or at least minimizes any testing triggered by a problem being uncovered, particularly by the customer. In addition, the present invention preferably provides a significant cost savings to the manufacturer and/or customer since by following a quality control and/or quality assurance system of the present invention, the amount of rejected batches of particulate material should be minimized, if not completely eliminated, due to such a quality control and/or quality assurance system. Thus, this is an additional benefit of the present invention.

As part of the present invention, in one or more embodiments of the present invention, the present invention relates to a quality control system which includes a test for determining at least one interfacial potential property value for a particulate material and also preferably a test for determining at least one morphological value for the same particulate material. The tests are described below. The quality control system can also include a device or medium to record at least one interfacial potential property value and optionally at least one morphological value for the particulate material. This recording can be done temporarily or permanently (e.g., in writing, electronically, and the like), such as on paper or with a computer program, such as Excel or any other types of software for recording data. Optionally, this data can then be compared from test to test to determine consistency. The present invention further relates to a method for quality control which includes analyzing at least one interfacial potential property of a particulate material on a routine basis to insure quality control. Furthermore, the present invention relates to a method for quality assurance which includes analyzing at least one interfacial potential property of a particulate material on a routine basis to insure quality assurance. The methods for quality assurance and/or quality control can further include analyzing at least one morphological value on a routine or non-routine basis to insure quality control and/or quality assurance.

Particulate materials are used in a variety of compounded systems, including, for example, dispersions in elastomers, polymers, solvents, resins, or mixtures thereof. Important aspects of performance include reinforcement, rheology control, formation of percolating networks, degree of dispersion, color, and conductivity. The properties of these compound systems are derived, in part, from the morphology of the particulate material used. Other physical phenomena involving particulate materials may respond to interfacial potential properties. Some also respond to the combination of both. Therefore, since interfacial potential plays an important role for particulate materials, along with morphology, the method of the present invention provides product consistency by maintaining both at least one morphological value as well as at least one interfacial potential property value of the particulate material. In this way, it has unexpectedly been found that product quality assurance (QA) and quality control (QC) are vastly improved if, along with measurements of morphology, measurements of values that reflect the interfacial potential of the particulate material are also made. Each of these will be described in more detail below.

The morphology of a particulate material is a description of its shape, size, and structure. The morphology can include particle size, surface area, particle porosity, aggregate size, aggregate shape, maximum packing density, powder bed porosity. In addition, the morphological value can include characteristics of a distribution, such as mean, standard deviation, width, skewness, etc., of such values as particle size, pore size, aggregate size, etc. A morphological value is the result of a measurement of one of these characteristics, or combinations thereof. The surface area per unit mass, the single particle diffusion constant, the average diameter of primary particles, and microstructure such as the diameters, shapes, and number of pores are examples of morphological values.

The interfacial potential of a particulate material is defined through a measure of a physical phenomenon that depends on the interaction of particulate material with other materials or with itself, after the effects of morphology have been removed. When two particles are in contact with each other the interfacial potential is the cohesion per unit area of contact. When particulate material is mixed into a fluid, the interfacial potential is the adhesion per unit area of the particle. If the measurement is per unit mass then the total interaction depends on the surface area per unit mass and the interfacial potential per unit area.

Examples of phenomena that relate solely to interfacial potential include the partitioning of particles between liquid phases, the spreading pressure of adsorbed gas, and the drop contact angle. These phenomena can be measured and the results applied without ambiguity as to whether the result is from morphology or interfacial potential since they only depend on interfacial potential.

However, as stated above, many useful physical phenomena respond to both morphology and interfacial potential. Examples include most aspects of rheology (e.g. yield, viscosity and shear thinning), the wicking rate of fluids in powder columns, and the maximum torque and the fluid volume at which it occurs in stirring wetted powders (i.e. the absorptometer or oil absorption test). For example, the rate a fluid rises in a column of packed particles depends upon both the pore size distribution of the column and the strength of the wetting interaction per unit area between the fluid and the particle surface. The volume at which the maximum torque occurs depends upon the maximum density to which the powder can be packed and the strength of the capillary forces in compressing the powder. The capillary forces, in turn, depend on the pore size and the interfacial potential per unit area. If the interaction is large enough and/or the pores small enough, the particulate material will be compressed to or nearly to its maximum density. Thus, for absorptometry on some particulate materials with some liquids, the characteristic volume is determined solely by particle morphology. For other liquids, volume and torque are determined by morphology and interfacial potential.

While these phenomena result from both morphological as well as interfacial potential effects, the way in which the measurements are analyzed, i.e., the calculation or algorithm used, will determine whether it is a morphological value or an interfacial potential property value. Thus, it is possible to use a test that responds to both morphology and interfacial potential and obtain independent information about both.

For example, a subset of physical phenomena that respond to both morphology and interfacial potential are ones where the only relevant aspect of the morphology is surface area and the dependence on area is known. Typical examples of this type of phenomena are adsorption studies where the partitioning of trace molecules between the surface and a gas or liquid phase is determined. For these physical phenomena the measurement is adjusted for surface area and the interfacial potential calculated.

Another subset of physical phenomena that responds to both morphology and interfacial potential are ones where the dependence on morphology and interfacial potential can be separated by mathematical analyses. For example the amount of gas adsorbed as a function of the pressure depends on the surface area and the interfacial potential. This function and the known size of the gas molecule can be used to calculate either the surface area or the interaction potential. The calculation of surface area using nitrogen gas is the so-called BET method. The usual calculation gives the surface area, an aspect of morphology, and the method is a morphological method. A different calculation gives the interfacial potential and the method is therefore an interfacial potential method.

Some physical phenomena may be separated into morphological effects and interfacial potentials by an algorithm. These provide a basis for measuring either morphology or interaction potential. The algorithm by which the data are interpreted determines which type of measurement it is.

A phenomenon that responds to both morphology and interfacial potential may be used as a quality assurance or quality control measurement method for interfacial potential if one of the following conditions is met.

A) if the effect of morphology can be eliminated by also measuring the physical phenomena with an inert probe. An inert probe is one for which the interfacial potential is negligible. For example, in inverse gas chromatography (IGC) the retention time of an inert probe is also measured.

B) if an external parameter, such as pressure or temperature, is changed and the response to that parameter allows an independent calculation of one or more morphology and interfacial potential values. For example, the BET analysis records adsorption as a function of pressure and two constants are calculated from the data. One constant measures surface area and one interfacial potential.

C) if the physical phenomenon is measured with the same particulate material in different fluids. The results are compared to determine differences when morphology of the particles is the same. The differences are derived from the different interfacial potentials. For example, the rate of wicking of various liquids can be compared to the rate of wicking of a hydrocarbon through a similarly packed powder bed.

D) if the number of different tests, which respond to both morphology and interfacial potential, exceeds the number of morphological parameters of concern minus those that have been determined by independent tests, then there are a sufficient number of independent tests to insure the consistency of the morphological parameters, plus at least a single aspect of the interfacial potential.

In all these, with the exception of D), the common purpose is to identify the portion of a physical phenomenon that depends on the interaction of particulate materials with other materials or with itself after the effects of morphology have been removed. This portion is the interfacial potential.

Therefore, in the method of the present invention, the steps of maintaining at least one morphological value and at least one interfacial potential property value with target ranges my utilize any of the techniques described above. Others are described in more detail below.

The method of the present invention may further comprise the step of maintaining at least one chemical value of the particulate material. The chemistry of a particulate material is the material's overall (or bulk) composition, surface composition, and/or extractable materials. The types, quantities, and arrangement of chemical moieties at the surface is called the surface chemistry. For example, the surface of carbon black may include carbon-oxygen surface groups, carbon-hydrogen surface groups, and/or other substituted carbon groups.

The chemical value of the particulate material can be determined using any technique known in the art. For example, the amounts of chemical moieties can be measured by desorption (for example, desorption of oxygen groups on carbon black), neutralization of surface groups by acids and bases, potentiometric, thermometric, and radiometric titrations, direct analysis by specific chemical reactions, polarography, infrared spectroscopy (IR), electron spin resonance (ESR), and X-ray photoelectron spectroscopy (XPS). The surface chemistry may be altered by chemical reactions or by removing extractable materials.

Examples of chemical values include, but are not limited to, pH and functional group levels. It has been found that, in general, measurements of chemical components, along with measurements of morphology, are not able to efficiently achieve the desired level of product consistency. Particulate surfaces can contain a large number of different types of chemical species, and therefore far too many species would have to be identified and their relative positions on the surface determined in order to obtain effective quality control and assurance. Furthermore, while methods exist for qualitative and quantitative analysis, surface positioning is currently beyond the state of the art.

For the method of the present invention, any particulate material may be used. The particulate material may be in any form such as a powder, a pellet, or a fluffy material. Examples of particulate materials include, but are not limited to, fillers, extenders, carbonaceous materials, carbon black, inorganic salts, silica (such as fumed silica, precipitated silica, or colloidal silica), silica aerogels, fumed oxides, silicates, silica sols including Stöber sols, metal oxides, hydrous metal oxides, iron oxides, aluminum oxides, boehmite, aluminum silicates, clays, kaolin, halloysite, montmorillonite, attapulgite, zeolites, ceramics (such as a metal carbide, a metal nitride, or a metal boride), calcium carbonate, chalk, barium sulfate, diatomaceous earth, asbestine, pigments (such as phthaolocyanines, Prussina blue, chromium oxide, and chrome green), zinc sulfide, zinc oxide, titania, antimony oxide, lead zinc, metals (such as tantalum, niobium, iron, aluminum, or silicon), and any of the above with surface treatments such as hydrophobic silicas, surface-modified carbon blacks, polymer treated powders, and laked pigments. Combinations or mixtures of these particulate materials may also be used. Examples of carbonaceous materials include, but are not limited to, carbon black, graphite, vitreous carbon, activated carbon, carbon fibers, nanotubes, graphite, and the like. Other examples include aggregates containing a carbon phase and a silicon-containing species phase or an aggregate containing a carbon phase with a metal-containing species phase. Also, coated particulate materials, such as silica-coated carbon black are other examples of particulate material. Furthermore, the carbonaceous material or other particulate material can be modified in any way such as having attached organic groups, polymer groups, and the like. Examples may include those described in U.S. Pat. Nos. 5,747,562, 5,830,930, 5,877,238, 5,904,762, 5,916,934, 5,919,841, 5,948,835, 6,008,272, 6,017,980, 6,028,137, 6,057,387, 6,197,274, 6,211,279, 6,323,273, 6,364,944, 6,448,309, all of which are incorporated in there entirety by reference herein.

The morphological values of the particulate materials in the method of the present invention can be determined using any method known in the art, such as colloidal techniques, including liquid or vapor adsorption, microscopy, or combinations of thereof. Typical liquid or vapor probes for adsorption include nitrogen, iodine, i ammonium bromide (CTAB), dibutyl phthalate (DBP), or paraffin oil. Examples of useful microscopy techniques include, but are not limited to, transmission electron microscopy (TEM), X-ray diffraction, dark field microscopy, oxidation studies, diffracted beam electron microscopy, phase contrast transmission electron microscopy imaging, high resolution scanning electron microscopy (SEM), scanning tunneling electron microscopy (STEM), scanning tunneling microscopy (STM), scanning force microscopy (SFM), and atomic force microscopy (AFM) imaging. Examples of colloidal techniques include, but are not limited to, masstone (blackness or color), tinting strength (ASTM D 3265), and the adsorption of nitrogen gas data (ASTM D 3037), cetyltrimethyl ammonium bromide (ASTM D 3765), or iodine (ASTM D 1510). The surface areas derived from each of the above mentioned methods can be affected in different ways by the amount and type of porosity, as well as the chemical nature of the surface of the particulate material. Porosity can be estimated from the apparent extra surface area detected in the adsorption of small probes, e.g., nitrogen, over large probes, e.g., CTAB. The aggregate size can be estimated by TEM, disc centrifuge photosedimentometry, sedimentation field flow fractionation, capillary hydrodynamic fractionation, dynamic light scattering, and differential mobility. Aggregate shape can be estimated by oil adsorption, particularly DBP, specific volume from density-pressure curves, and TEM.

Examples of morphological properties and tests used to measure them are shown in Table 1 below. These morphological values may be used alone or in combination with other morphological values.

TABLE 1

| Morphological Property | Testing Method |
|---|---|
| Particle size and distribution | Transition electron microscopy (TEM) Calculation from surface area Masstone |
| Surface area | Nitrogen adsorption (ASTM D 3037) Iodine adsorption (ASTM 1510) CTAB adsorption (ASTM D 3765) Carman surface area |
| Pore size and distribution | Difference between nitrogen and CTAB surface areas |
| Aggregate size and distribution | TEM Light scattering Disc centrifuge |
| Aggregate shape | TEM Oil absorption DBP absorptometry Specific volume from density-pressure curves |

The morphological value is maintained within a first target range. This range will depend on the particular morphological property being measured. Preferably, the first range is based on a defined specification. For example, the first target range may be a range that is within about 10% (above or below) of the target morphological value. Tighter specification ranges may also be used, such as within about 8%, within about 5%, or within about 0.5% to about 3% of the target value. The target range may also be a specified value that the morphological value must either not exceed (a value that is less than the target) or must not be below, depending on the specific morphological value and test. The target value can be determined based on the desired customer performance.

As described above, the interfacial potential property value may be any property that can be correlated to the interfacial potential of the particulate material. For purposes of the present invention, and as described in more detail below, results from tests that can be used to determine the interfacial potential, or to permit a way to assign a value which is affected by the interfacial potential properties of a particulate material are considered to be the interfacial potential property value in the present invention. These may be determined using a variety of techniques known in the art, including the following:

Interfacial potential by masstone. The optical density of a particulate material, such as a pigment, in a matrix depends on its intrinsic properties and how the particulate material is dispersed throughout the matrix. If poorly dispersed, then the optical density is low. If well dispersed, the optical density is high. The dispersibility of a particulate material depends on both its morphology and on its interfacial potential. Therefore the masstone depends on the interfacial potential of the pigment. The difference in masstone for the same particulate material dispersed under the same conditions in different matrices can be used as a QA/QC method for interfacial potential.

Interfacial potential by gas adsorption techniques. Some of the methods described above for determining surface area from the adsorption of gases, e.g., BET analysis, fit the data with two parameters—one for the surface area and one for the solid-gas interaction. The parameter for the solid-gas interaction is a measure of interfacial potential. Therefore from the same data that is used to report surface area by BET analysis, information about the interfacial potential is available. Therefore, a method which involves measuring the adsorption of gases other than nitrogen or krypton, which are common "inert" gases used for BET analysis, can be used for determining interfacial potential. Examples of alternative gases which can be used for measuring interfacial potential include water, ammonia, and various organic vapors such as toluene, ethanol, and the like. A preferred gas adsorption technique and data analysis to obtain interfacial potentials is to measure the spreading pressure, which is described in more detail below.

Interfacial potential from adsorption from solution. Adsorption from solution is a similar technique to the adsorption of gases. Many solutes are surface active, that is, they preferentially accumulate at the surface of a particulate material when it is mixed into a solution. The amount of adsorption depends on the surface area, the morphology, and the interfacial potential. If the amount of adsorption of two or more different surface active solutes are measured on the same particulate material, then sufficient information is gathered to be sensitive independently to the morphology and interfacial potential, and would therefore be useful as a method for determining interfacial potential.

Interfacial potential from light scattering or disc centrifuge. To obtain aggregate size by light scattering, a particulate material must be highly diluted into a liquid. Often a surfactant is added to insure that the particulate material is well separated and does not flocculate during the time of measurement, allowing for an accurate measure of size. A variation of this test would give information about interfacial potential, especially the cohesion of the particulate material. For this method, the particle size would be measured as a function of time with no surfactant added. A dispersion, even when highly dilute, will flocculate with time. The rate of flocculation is a measure of the cohesion of the particulate material. Therefore a measure of the particle size or the particle size distribution as a function of time is a measure of the interfacial potential, and, in particular, cohesion.

Interfacial potential by oil absorption. A common type of QA/QC test for the structure of particulate materials such as carbon black is to add a liquid slowly to a mass of material as it is being stirred. As the ratio of the volume of liquid to the mass of particulate material increases, the torque required to mix changes. Typically, the ratio of the volume of liquid added to the mass of material at the maximum torque is reported as a QA/QC test for structure. Another QA/QC test is to report the same ratio at a predetermined fraction of the maximum torque. A preferred liquid is dibutyl phthalate (DBP), and the reported value is often referred to as the DBP number. Paraffin oil has also been used. These volumes to mass ratios are strong functions of the morphology of the particulate material.

However, the flow of a particulate material wetted by a liquid also depends on the interfacial potential through the relative strengths of particle-particle interactions and particle-liquid interactions. When an absorptometer test is repeated with a second liquid on the same particulate material, the relation between torque and volume of liquid added changes. For example, maximum torque may be different for the same particulate material in different liquids, or, alternatively, the volume of liquid added to reach the maximum torque may be different. These differences reflect the interfacial potential of the particulate materials. Therefore combinations of oil absorption tests with different liquids can be used as QA/QC tests for interfacial potential of a particulate material.

Interfacial potential by wicking rates. When a particulate material is packed into a column and the bottom of the packed bed contacts a liquid, the liquid will wick up through the packed bed. The wicking rate depends on the packing of the particulate material (which depends on morphology) and the strength of interaction between the particulate material and the liquid (which depend on interfacial potential). The difference in wicking rate for two or more liquids into equivalent packed columns of the same particulate material can be used as a measure of the interfacial potential of the particulate material.

Interfacial potential by rheological tests. The degree of flocculation of a particulate material in a liquid depends on the balance between the particle-particle interactions and the particle-liquid interactions. In other words, the degree of flocculation depends on the interfacial potential of the particulate material. One measure of this balance is the degree of shear thinning—the drop in viscosity with an increase in shear rate. Another measure of the degree of flocculation is the Bingham yield point. Yet another measure of the degree of flocculation, is the elastic modulus at low strains. Each of these methods can be used for determining the interfacial potential of the particulate material.

Interfacial potential by sedimentation volumes. As dispersions flocculate, particle settling occurs because the size of the particles increases. If the particle-particle energies are strong compared to the particle-liquid energies, the flocs are large and the sediment height high. Therefore measures of the sediment height of flocculated dispersions of particulate material can be used as a measure of the interfacial potential.

Interfacial potential by phase segregations. When a particulate material is added to a container with two or more immiscible liquids, the material can preferentially accumulate in one of the phases or at the phase boundary. This preferential segregation is a consequence of the interfacial potential of the particulate material and can therefore be used as a QA/QC test.

Interfacial potential by inverse gas chromatography. Inverse gas chromatography (IGC) is the measurement of the retention times of gas probes flowing through packed beds of particulate materials. The stronger the interfacial potential, the longer the retention time. The retention time also depends on the morphology and packing of the particulate material. Thus, in a typical procedure, the retention times of organic vapors are compared with those of hydrocarbons. This analysis provides a measure of the interfacial potential of the particulate material and can therefore be used as a QA/QC test.

Interfacial potential by spreading pressure. The spreading pressure of a gas on a particulate material is a measure of the interfacial potential. It can be calculated from the gas adsorption isotherm (moles adsorbed as a function the partial pressure of the gas). The spreading pressure is the integral under the adsorption curve when the partial pressure is plotted as a logarithm. If the data is reported as moles adsorbed per unit mass, the spreading pressure is energy per unit mass. The calculated spreading pressure can be divided by the specific surface area to give the interfacial potential in units of energy per unit area. A wide variety of gases can be used, including, for example, tetrahydrofuran, water, ethanol, toluene, methylethyl ketone, cyclohexanone, and the like. Calculating the spreading pressure of a particulate material for each gas provides a measure of the interfacial potential.

Other methods for determining the interfacial potential of the particulate material can be used and will be known to one skilled in the art. Examples include:

a) by compressing the particulate material to give a flat surface upon which the contact angle of a probe liquid can be measured;

b) by measuring the pressure of gas to remove a probe liquid from the pores of a packed bed of the particulate material after it has been filled or partly filled by the liquid;

c) by measuring the centrifugal force necessary to immerse particles of the particulate material floating on a probe liquid;

d) by measuring the two-dimensional pressure sufficient to force particles of the particulate material floating on a probe liquid in a Langmuir trough;

e) by measuring the relative adsorption of dye probes;

f) by measuring the heat when the particulate material is immersed into a probe liquid;

g) by measuring the heat released when a test adsorbate is adsorbed by the particulate material. This may be done in a flow calorimeter with the adsorbate dissolved in a carrier liquid, or in a batch calorimeter where the adsorbate is either a neat liquid or a solution.

h) by measuring the sediment volumes in an homologous series of test liquids, as described in Morrison, I. D.; Ross, S. Colloidal Dispersions: Suspensions, Emulsions, and Foams; John Wiley & Sons: New York; 2002, pp 505-515, which is incorporated in its entirety by reference herein;

i) by determining the composition of a solvent mixture just sufficient to immerse floating particles of the particulate material;

j) by measuring the deviations in viscosity from the Einstein equation for the flow of hard spheres or other deviations from the behavior of hard sphere dispersions at higher concentrations.

In addition, the interfacial potential property values may be used either alone or in combination with other interfacial potential property values.

The interfacial potential property value is maintained within a second target range. As with the first range for the morphological value described above, the second range will depend on the particular property related to the interfacial potential that is being measured, and may be the same or different as the first range for the morphological value. For example, the second target range may be a range that is within about 50% (above or below) of the target interfacial potential property value. Tighter specification ranges may also be used, such as within about 25%, within about 10%, within about 8%, within about 5%, or within about 0.5% to about 3% of the target value. The target range may also be a specified value that the interfacial potential property value must either not exceed (a value that is less than the target) or must not be below, depending on the specific interfacial potential property value and test. The target value can be determined based on the desired customer performance.

As stated above, the method of the present invention provides product consistency by preferably maintaining both a morphological value and an interfacial potential property value within target ranges. In one embodiment, the step of maintaining either value comprises determining, measuring, or analyzing for at least one morphological value and/or interfacial potential property value of the particulate material and adjusting at least one process variable of the process for producing the particulate material. The adjustment is made so that the desired value (either the morphological value or the interfacial potential property value, or both) are maintained within the corresponding target range. Preferably, the adjustment is made during the process for producing the particulate material. Thus, product is prepared, the properties are measured, the results are compared to the target values, and the process is accordingly adjusted, if necessary, so as to produce material having the desired property values. This is preferably done prior to the product being shipped to a customer.

A variety of different process variables can be adjusted in order to maintain the morphological value, the interfacial potential property value, or both. The variable will depend on the type of particulate material. For examples, adjustable process variable for a particulate material comprising carbonaceous material and, in particular, carbon black include, but are not limited to combustion stoichiometry, reactor quench length, feedstock composition, primary fuel type, level of downstream additive (including oxidants and chemical reagents), and post treatment conditions. Examples of post treatments include those described in U.S. Pat. Nos. 5,554,739, 5,630,868, 5,672,198, 5,698,016, 5,707,432, 5,713,988, 5,803,959, 5,837,045, 5,851,280, 5,885,335, 5,895,552, 5,900,029, 5,922,118, 5,968,243, 6,042,643, and 6,494,946, each incorporated in their entirety by reference herein. If the particulate material comprises metal oxide, such as fumed silica, adjustable process variables would include combustion stoichiometry, amount of quench air, feedstock composition, primary fuel type, level of downstream additives, and post treatment conditions (including chemical modification).

The present invention will be further clarified by the following examples which are intended to be only exemplary in nature.

EXAMPLES

Example 1

Standard grades of carbon black are available from various manufacturers. One of the Q/C specifications for these standard grades is the DBP number. The volume at maximum torque for dibutyl phthalate (DBP) is a QA/QC measure of the morphology of the carbon black.

The DBP value was measured on six standard grades in a Brabender mixer with a device having a means for recording the torque data. The data is reported in the Table 2 below. The carbon blacks are ordered by their DBP numbers.

Determining the volume at maximum torque for another liquid is an example of a QA/QC test for the interfacial potential of the carbon black. For this example, water, a 60/40 ethylene glycol/water mixture (60 parts ethylene glycol by volume to 40 parts water by volume), ethylene glycol, and paraffin oil were used. The volumes at maximum torque are also shown in Table 2. These results show that standard grades order differently depending on which liquid is used as a QA/QC probe liquid. For example, looking at the data for water, as the DBP number increases, the interfacial potential property value may increase or decrease. When these carbon blacks are used in applications where both structure and interfacial potential are the significant factors, the product properties may therefore vary unexpectedly.

TABLE 2

| | Volume @Max T for 5 liquids | | | | |
|---|---|---|---|---|---|
| Sample name | Water | 60% glycol | 100% glycol | DBP | Paraffin Oil |
| ASTM Reference Black A6 | 205.5 | 152.6 | 128.3 | 128.7 | 130.65 |
| ASTM Reference Black B6 | 238 | 142.3 | 119.5 | 121.7 | 123.75 |
| ASTM Reference Black C6 | 154.55 | 94.6 | 74.9 | 80.4 | 83.05 |

TABLE 2-continued

| | Volume @Max T for 5 liquids | | | | |
|---|---|---|---|---|---|
| Sample name | Water | 60% glycol | 100% glycol | DBP | Paraffin Oil |
| ASTM Reference Black D6 | 122.2 | 81.5 | 69.8 | 74.05 | 75.9 |
| ASTM Reference Black E6 | 150.8 | 103.3 | 88.9 | 95.25 | 98.1 |
| ASTM Reference Black F6 | 227.3 | 156.2 | 133.9 | 137.9 | 139.6 |

Example 2

Manufacturers often produce the same product at different manufacturing plants. The products need to meet the same QA/QC standards regardless of where they are produced.

Table 3 shows data taken on the same grade of carbon black from four manufacturing plants. In this example the "% of max DBP" is the percentage of the maximum DBP value in the table, which was that of Plant E. The DBP numbers were measured as the volume at maximum torque on a Brabender abosrptometer with a device capable of recording the torque data. Note that the DBP values are nearly identical (within approximately 96% of the maximum value). The DBP values are part of the current QA/QC test and by this criterion, all the samples would therefore be considered to be the same.

The volume at maximum torque was also measured for three other liquids: ethylene glycol (EG), 60/40 ethylene glycol/water (60 parts ethylene glycol by volume and 40 parts water by volume), and pure water. This is an example of an interfacial potential property QA/QC test.

TABLE 3

| | Volume @Max Torque | | | |
|---|---|---|---|---|
| Sample name | % of max DBP | EG | 60% EG | Water |
| Plant A | 97 | 77.1 | 108.8 | 17.15 |
| Plant B | 98.8 | 71.95 | 92.9 | 132.15 |
| Plant C | 97.8 | 72.8 | 90 | 138.35 |
| Plant D | 95.8 | 82.3 | 115.4 | 145.8 |
| Plant E | 100 | 73.5 | 91.9 | 100.35 |

As the data in Table 3 shows, the volumes obtained for the other liquids are not the same from manufacturing plant to manufacturing plant. This means that the interfacial potentials are not the same for the four samples and hence the products are not the same.

Example 3

The carbon black of Example 2 had a low DBP value. A similar test was done for a grade of carbon black with a higher DBP specification. Samples were taken from three manufacturing plants. Again the volume at maximum torque with DBP was measured in a Brabender absorptometer with a device having a means of recording the torque data, and the results are shown as a percentage of the maximum value (Plant F). Results are shown in Table 4 below. The volume at maximum torque was also measured with ethylene glycol (EG), 60/40 EG/water (60 parts ethylene glycol by volume and 40 parts water by volume), and pure water, and the resulting data are also shown in Table 4.

TABLE 4

| Sample name | % of max DBP | Volume @Max Torque | | |
|---|---|---|---|---|
| | | EG | 60% EG | Water |
| Plant F | 100 | 115.3 | 150.5 | 217.1 |
| Plant G | 98.3 | 114.0 | 141.5 | 183.95 |
| Plant H | 97.2 | 111.5 | 138.9 | 208.2 |
| Plant I | 97.5 | 114.1 | 139.6 | 226.75 |

The data shows that when an interfacial potential QA/QC test is performed, the grades made in different plants are found to be different.

Example 4

Modern carbon black manufacturing plants can be run under a variety of process conditions and still produce product that has nearly the same standard QA/QC values (Analytical Properties), such as iodine numbers (I2 Number), DBP number (DBPA), nitrogen surface area (N2SA), t-area (STSA), and tint. The upper rows in the Table 5 below shows that by the standard QA/QC values, the listed carbon blacks are the same. However, when the interfacial potentials are measured by the rate of wicking of various liquids up a packed powder bed, using the Bartell method (which is described in Morrison, I. D.; Ross, S. Colloidal Dispersions: Suspensions, Emulsions, and Foams: John Wiley & Sons: New York; 2002; pp 210-212, incorporated in its entirety by reference herein), significant differences can be seen. The wicking rates have units of $g^2/s$.

Thus, while these particulate materials are all the same by the usual QA/QC tests, they differ by their interfacial potentials, and the method of the present invention, which comprises steps of maintaining at least one morphological value and at least one interfacial potential property value, would be able to distinguish between them.

Example 5

The previous examples have used a single interfacial potential parameter from each test. However combinations of multiple parameters can also be used.

An absorptometer (available from C. W. Brabender Instruments, Inc., 50 E. Wesley St., South Hackensack, N.J. 07606) was used following the procedure described in ASTM test D-2414-01. Dibutyl phthalate (DBP) was added by means of a constant-rate buret to a sample of carbon black in the mixer chamber. A torque sensor detected the rise in viscosity from the free-flowing powder to the semi-plastic flow of the continuous mass. The absorptometer and buret were shut off when the torque passed through its characteristic maximum in such a fashion that there was assurance that the maximum torque had been reached. The volume of DBP per unit mass of carbon black was recorded as the DBP absorption number. CDBP values were obtained using a similar test in which the carbon black was pre-compressed before conducting the test. (ASTM D-3493)

This data is shown in Table 6, along with the iodine number and nitrogen, and STSA surface area values. These morphological values are reported as a percentage of the maximum values in the table. Note that, based on all of the values shown and, in particular, the values for the standard liquid DBP, these materials would be considered identical.

TABLE 5

| Analytical Properties | | | | | | |
|---|---|---|---|---|---|---|
| I2 Number | 71 | 85.3 | 88 | 86.5 | 88.6 | 85.7 |
| DBPA | 108 | 106.9 | 108.2 | 106.5 | 108.1 | 104.9 |
| N2SA | 61.8 | 75.6 | 76 | 75.7 | 75.7 | 73.9 |
| STSA | 61.4 | 74.7 | 71.7 | 72.2 | 69.6 | 69.4 |
| Tint | 89.3 | 105.5 | 99.2 | 98 | 99.3 | 104 |
| Wicking Rates | | | | | | |
| Water | 0.0005 | 0.0011 | 0.0011 | 0.0007 | 0.0009 | 0.0006 |
| Formamide | 0.0044 | 0.0062 | 0.0049 | 0.0039 | 0.0063 | 0.0049 |
| Ethylene Glycol | 0.0023 | 0.0011 | 0.0012 | 0.0008 | 0.0016 | 0.0011 |
| Bromonaphthalene | 0.0060 | 0.0023 | 0.0031 | 0.0017 | 0.0021 | 0.0017 |
| Pentane | 0.0212 | 0.0046 | 0.0077 | 0.0029 | 0.0074 | 0.0091 |
| Tetrahydrofuran | 0.0094 | 0.0055 | 0.0125 | 0.0047 | 0.0185 | 0.0065 |
| Analytical Properties | | | | | | |
| I2 Number | 85.8 | 85.8 | 82.2 | 85.9 | 87.9 | |
| DBPA | 104.4 | 105.9 | 104.5 | 102.9 | 107.8 | |
| N2SA | | 76.1 | 73.6 | 74.6 | 77 | |
| STSA | | 72.8 | 70.3 | 70.1 | 71.3 | |
| Tint | 98.1 | 94.1 | 98.3 | 102.9 | 94.8 | |
| Wicking Rates | | | | | | |
| Water | 0.0007 | 0.0006 | 0.0006 | 0.0009 | 0.0010 | |
| Formamide | 0.0054 | 0.0029 | 0.0025 | 0.0045 | 0.0050 | |
| Ethylene Glycol | 0.0016 | 0.0007 | 0.0004 | 0.0012 | 0.0015 | |
| Bromonaphthalene | 0.0017 | 0.0017 | 0.0011 | 0.0020 | 0.0020 | |
| Pentane | 0.0070 | 0.0038 | 0.0028 | 0.0049 | 0.0085 | |
| Tetrahydrofuran | 0.0138 | 0.0062 | 0.0032 | 0.0090 | 0.013 | |

TABLE 6

| Sample | % of max DBP number (cc/100 g) @70% | % of max CDBP (cc/100 g) @70% | % of max $I_2$No (mg/g) | % of max BET surface area ($m^2/g$) | % of max STSA ($m^2/g$) |
|---|---|---|---|---|---|
| CB-A | 100 | 100 | 91.1 | 97.6 | 95.1 |
| CB-B | 99.2 | 96.4 | 95.6 | 95.1 | 92.7 |
| CB-C | 98.3 | 96.3 | 95.6 | 97.6 | 97.6 |
| CB-D | 99.2 | 94.0 | 97.8 | 100 | 100 |
| CB-E | 98.3 | 100 | 100 | 100 | 97.6 |

A similar absorptometry procedure was followed, using paraffin oil, ethylene glycol, water, and a 60/40 mixture of ethylene glycol and water. Results are show in FIG. 1. As can be seen, the values for the measured parameters in ethylene glycol are different for each sample. The same is true for the paraffin oil. Significant separations between the morphologically identical samples of carbon black are found when a 60/40 ethylene glycol/water mixture (60 parts ethylene glycol by volume and 40 parts water by volume) or just pure water is used. In addition, the ordering of the samples (the carbon black samples that represent the high and low values are shown in FIG. 1) changes depending on the solvent used. Thus, FIG. 1 shows that samples of carbon black that were the same by standard morphology tests are shown to be different from each other when tested using different liquids. Therefore, these values can be used as a QC/QA method for the carbon black and would provide better product consistency than the typical morphological values alone. Additional use of any of the morphological values would provide for even better product consistency.

Other embodiments of the present invention will be apparent to those skilled in the art from consideration of the present specification and practice of the present invention disclosed herein. It is intended that the present specification and examples be considered as exemplary only with a true scope and spirit of the invention being indicated by the following claims and equivalents thereof.

What is claimed is:

1. A method of providing product consistency for a particulate material comprising the steps of:
   a) determining and maintaining at least one morphological value of a particulate material within a first target range and
   b) maintaining at least one interfacial potential property value of the particulate material within a second target range, comprising:
      i) determining at least one interfacial property value of the particulate material; and
      ii) adjusting at least one process variable of a process for producing the particulate material, wherein the adjustment maintains the interfacial potential property value within the second target range, wherein said particulate material is a carbon black or silica, and wherein said particulate material has said morphological value and said interfacial potential property value.

2. The method of claim 1, further comprising the step of maintaining at least one chemical value of the particulate material.

3. The method of claim 2, wherein the chemical value is pH or functional group level.

4. The method of claim 1, wherein the particulate material is fumed silica.

5. The method of claim 1, wherein the morphological value is surface area, particle size, structure, porosity, or combinations thereof.

6. The method of claim 1, wherein the first target range for the morphological value is within about 10% of the morphological value.

7. The method of claim 1, wherein the second target range for the interfacial potential property value is within about 50% of the interfacial potential property value.

8. The method of claim 1, wherein the step of maintaining at least one morphological value of a particulate material comprises
   i) determining at least one morphological value of the particulate material; and
   ii) adjusting at least one process variable of a process for producing the particulate material, wherein the adjustment maintains the morphological value within the first target range.

9. The method of claim 8, wherein the morphological value is determined during the process for producing the particulate material.

10. The method of claim 8, wherein the morphological value is determined prior to shipping the particulate material to a customer.

11. The method of claim 1, wherein the interfacial potential property value is determined during the process for producing the particulate material.

12. The method of claim 1, wherein the interfacial potential property value is determined prior to shipping the particulate material to a customer.

13. The method of claim 8, wherein the morphological value is determined by liquid adsorption, vapor adsorption, microscopy, or combinations thereof.

14. The method of claim 8, wherein the morphological value is determined by an adsorption method using iodine, nitrogen, CTAB, DBP, or paraffin oil.

15. The method of claim 8, wherein the process variable is selected from the group consisting of: combustion stoichiometry, reactor quench length, feedstock composition, primary fuel type, level of downstream additives, and post treatment conditions.

16. The method of claim 1, wherein the interfacial potential property value is determined by an interfacial potential absorptometry method comprising performing an absorptometer test on the particulate material with first and second different liquids and measuring maximum torque or volume of liquid added for the different liquids.

17. The method of claim 16, wherein the interfacial potential absorptometry method uses a liquid other than DBP or paraffin oil.

18. The method of claim 16, wherein the interfacial potential absorptometry method uses water, ethylene glycol, or mixtures thereof.

19. The method of claim 1, wherein the interfacial potential property value is determined by a wicking rate method comprising determining a difference in wicking rate for two or more liquids into equivalent packed columns of the particulate material.

20. The method of claim 1, wherein the interfacial potential property value is determined by a yield point method comprising measuring a degree of flocculation of the particulate material.

21. The method of claim 1, wherein the interfacial potential property value is determined by a interfacial potential vapor adsorption method comprising using a gas for gas adsorption analysis, wherein said gas is selected from water gas, ammonia gas, toluene gas, or ethanol gas.

22. The method of claim 1, wherein the interfacial potential property value is determined by an IGC method.

* * * * *